US009839744B2

(12) United States Patent
Muto et al.

(10) Patent No.: US 9,839,744 B2
(45) Date of Patent: Dec. 12, 2017

(54) OCCLUSION DETECTION DEVICE, TRANSFUSION APPARATUS, AND OCCLUSION DETECTION METHOD

(71) Applicant: MINEBEA CO., LTD., Kitasaku-Gun, Nagano (JP)

(72) Inventors: Akira Muto, Fujisawa (JP); Hiroyuki Ohmae, Kawasaki (JP); Kiyoshi Omori, Machida (JP)

(73) Assignee: Minebea Co., Ltd., Nagano (JP)

( * ) Notice: Subject to any disclaimer, the term of this patent is extended or adjusted under 35 U.S.C. 154(b) by 36 days.

(21) Appl. No.: 14/753,292

(22) Filed: Jun. 29, 2015

(65) Prior Publication Data

US 2015/0374903 A1 Dec. 31, 2015

(30) Foreign Application Priority Data

Jun. 30, 2014 (JP) .................. 2014-134269

(51) Int. Cl.
*A61M 5/142* (2006.01)
*A61M 5/168* (2006.01)

(52) U.S. Cl.
CPC .... *A61M 5/14228* (2013.01); *A61M 5/16854* (2013.01); *A61M 2005/16863* (2013.01);
(Continued)

(58) Field of Classification Search
CPC ......... A61M 2005/16868; A61M 2005/16863; A61M 5/16854; A61M 5/14228;
(Continued)

(56) References Cited

U.S. PATENT DOCUMENTS 5,096,385 A 3/1992 Georgi et al.
5,103,211 A * 4/1992 Daoud .............. A61M 5/16859
128/DIG. 13
(Continued)

FOREIGN PATENT DOCUMENTS

JP H05-031176 A 2/1993
JP 10-071202 A 3/1998
(Continued)

OTHER PUBLICATIONS

A Rejection Decision issued in the corresponding Japanese patent application No. 2014-134269, dated Feb. 17, 2016.
(Continued)

*Primary Examiner* — Bhisma Mehta
*Assistant Examiner* — Brandy S Lee
(74) *Attorney, Agent, or Firm* — Carrier Blackman & Associates, P.C.; Joseph P. Carrier; Jeffrey T. Gedeon

(57) ABSTRACT

An occlusion detection device detects an occlusion of a flexible fluid path on either of upstream and downstream sides of a pump mechanism, the pump mechanism transporting a liquid through the fluid path by elastically deforming the fluid path. The occlusion detection device is provided with: an occlusion sensor that is disposed on the downstream side of the pump mechanism and detects an internal pressure of the fluid path during a liquid transporting operation of the pump mechanism; and a data processing circuit that analyzes on which side of the upstream and downstream sides of the pump mechanism the occlusion of the fluid path occurs, based on a change of the internal pressure of the fluid path detected by the occlusion sensor and outputs an analysis result.

6 Claims, 9 Drawing Sheets

(52) U.S. Cl.
CPC .............. *A61M 2005/16868* (2013.01); *A61M 2005/16872* (2013.01)

(58) Field of Classification Search
CPC .............. A61M 5/14232; A61M 5/142; A61M 5/16831; A61M 2005/16872; A61M 5/16859; A61M 5/168; F04B 43/12
See application file for complete search history.

(56) References Cited

U.S. PATENT DOCUMENTS

| | | | | |
|---|---|---|---|---|
| 5,807,322 | A | * | 9/1998 | Lindsey ............ A61M 5/16859 604/65 |
| 5,827,223 | A | | 10/1998 | Butterfield |
| 2005/0278072 | A1 | * | 12/2005 | Gaines .............. A61M 5/14232 700/282 |
| 2011/0224603 | A1 | | 9/2011 | Richter |
| 2012/0079886 | A1 | * | 4/2012 | Beck ................. A61M 5/16854 73/756 |
| 2012/0203179 | A1 | * | 8/2012 | Hills ................. A61M 5/16854 604/151 |

FOREIGN PATENT DOCUMENTS

| | | |
|---|---|---|
| JP | H11500338 A | 1/1999 |
| JP | 11-137679 A | 5/1999 |
| JP | H11-342199 A | 12/1999 |
| JP | 2006-223448 A | 8/2006 |
| JP | 2007-061389 A | 3/2007 |
| JP | 2012503183 A | 2/2012 |
| JP | 2012-082730 A | 4/2012 |
| WO | 9707843 A1 | 3/1997 |

OTHER PUBLICATIONS

Office Action dated Jul. 29, 2015 in the corresponding Japanese Patent Application No. 2014-134269 without English translation.

* cited by examiner

OCCLUSION DETECTION DEVICE, TRANSFUSION APPARATUS, AND OCCLUSION DETECTION METHOD

BACKGROUND OF THE INVENTION

1. Field of the Invention

The present invention relates to an occlusion detection device which detects an occlusion of a fluid path for transporting a liquid, mainly a tubular body (in which the outer shape is deformable by a change of the internal pressure, such as a flexible tube), a transfusion apparatus including the device, and an occlusion detection method.

2. Description of the Related Art

A conventional technique for detecting an occlusion of a tubular body can be found in, for example, in JP-A-11-137679.

The technique is used for detecting an occlusion of a transfusion tube through which a medical solution is transported. In the technique for detecting an occlusion of a transfusion tube, an occlusion of a transfusion tube is detected by a device including: a pair of occlusion sensors which detect an occlusion of the transfusion tube on the upstream and downstream sides of a pump mechanism; a unit which sets an occlusion detection pressure; and a comparing unit which compares a detection value that is detected by one of the paired occlusion sensors, with the occlusion detection pressure.

In the prior art technique, however, an occlusion of the transfusion tube is detected on each of the upstream and downstream sides of the pump mechanism, and therefore it is necessary to dispose one occlusion sensor on each of the upstream and downstream sides of the pump mechanism, or a total of two occlusion sensors. Consequently, the number of components and that of assembling steps are increased to raise the production cost, and moreover the space occupied by the components is large.

SUMMARY

The present invention has been made in view of above circumstances, and one of the objects of the present invention is to provide an occlusion detection device, transfusion apparatus, and occlusion detection method in which an occlusion sensor is required only on the downstream side of a pump mechanism, the number of components and that of assembling steps can be decreased to lower the production cost, and the space occupied by the components can be reduced, whereby the size of the device can be made small.

According to an illustrative embodiment of the present invention, there is provided an occlusion detection device that detects an occlusion of a flexible fluid path on either of upstream and downstream sides of a pump mechanism, the pump mechanism transporting a liquid through the fluid path by elastically deforming the fluid path, the occlusion detection device including: an occlusion sensor that is disposed on the downstream side of the pump mechanism and detects an internal pressure of the fluid path during a liquid transporting operation of the pump mechanism; and a data processing circuit that analyzes on which side of the upstream and downstream sides of the pump mechanism the occlusion of the fluid path occurs, based on a change of the internal pressure of the fluid path detected by the occlusion sensor and outputs an analysis result.

According to another illustrative embodiment of the present invention, there is provided a transfusion apparatus including: a pump mechanism that transports a liquid through a fluid path by elastically deforming the fluid path; and an occlusion detection device that detects an occlusion of the fluid path on either of upstream and downstream sides of the pump mechanism. The occlusion detection device includes: an occlusion sensor that is disposed on the downstream side of the pump mechanism and detects an internal pressure of the fluid path during a liquid transporting operation of the pump mechanism; and a data processing circuit that analyzes on which side of the upstream and downstream sides of the pump mechanism the occlusion of the fluid path occurs, based on a change of the internal pressure of the fluid path detected by the occlusion sensor and outputs an analysis result.

According to still another illustrative embodiment of the present invention, there is provided an occlusion detection method for detecting an occlusion of a flexible fluid path on either of upstream and downstream sides of a pump mechanism, the pump mechanism transporting a liquid through the fluid path by elastically deforming the fluid path. The method includes: detecting an internal pressure of the fluid path at the downstream side of the pump mechanism during a liquid transporting operation of the pump mechanism; and analyzing on which side of the upstream and downstream sides of the pump mechanism the occlusion of the fluid path occurs based on a change of the internal pressure of the fluid path at the downstream side.

According to still another illustrative embodiment of the present invention, there is provided an occlusion detection device including: an occlusion sensor that is disposed at a fluid path on a downstream side of a pump mechanism and detects an internal pressure of the fluid path, the pump mechanism transporting a liquid through the fluid path by elastically deforming the fluid path; and a processor that detects an occlusion occurred on an upstream side or on the downstream side of the pump mechanism based on the internal pressure detected by the occlusion sensor.

DETAILED DESCRIPTION

Hereinafter, embodiments of the invention will be described. Prior to the description, first, the background and summary of the invention will be described.

In transfusion apparatuses (infusion pumps) which are used in the medical field, a peristaltic pump mechanism is widely employed as a pump mechanism for transporting a liquid such as a medical solution or a dialysis solution through a transfusion tube. In peristaltic pump mechanisms, there are the finger type in which a plurality of fingers (projections) are disposed, and the roller type in which a plurality of columnar rollers are disposed. A transfusion tube (hereinafter, often referred to merely as a tube) is held by being pressed between the fingers or the rollers and a pressing plate. During the liquid transporting operation, the side surface of the tube is pressed so as to be squeezed by a peristaltic motion caused by advancing/retracting operations of the fingers or rotations of the rollers, to be elastically deformed, thereby transporting a medical solution or the like in the tube in a given direction.

An example of a pump mechanism of the finger type is disclosed in JP-A-11-137679 above, and an example of a pump mechanism of the roller type is disclosed in JP-A-2006-223448 and JP-A-2012-082730.

As, a pump mechanism of the type other than the peristaltic type, there is proposed a pump mechanism as such disclosed in JP-A-10-071202. In this type of pump mechanism, a chamber having a flexible wall is disposed in the middle of a fluid path, and a liquid is transported by reciprocating the chamber by a plunger or the like.

The present invention may be applied to a transfusion apparatus in which a liquid is transported by pressing a flexible fluid path.

In such a transfusion apparatus, a transfusion in a tube stagnates because of clogging of a foreign material or bacteria, filter disposed in the middle of the tube, bending of the tube, clogging of a needle connected to the tube, or the like, or namely clogging may occur in the tube. A transfusion apparatus has various safety functions in order to rapidly deal with such an occlusion. First, an occlusion should be detected so as to cause the safety function to operate. Therefore, the detection of an occlusion is performed. An occlusion may occur on either of the upstream and downstream sides of the pump mechanism. Consequently, the detection of tube occlusion is usually performed on both the upstream and downstream sides of the pump mechanism. The term "upstream and downstream sides" (the upstream side, the downstream side) means the upstream side or downstream side with respect to the pump mechanism.

Conventionally, the detection of tube occlusion is performed by one occlusion sensor disposed on each of the upstream and downstream sides of the pump mechanism, or a total of two occlusion sensors. Therefore, the above-discussed problems may be caused.

Figure 1A:
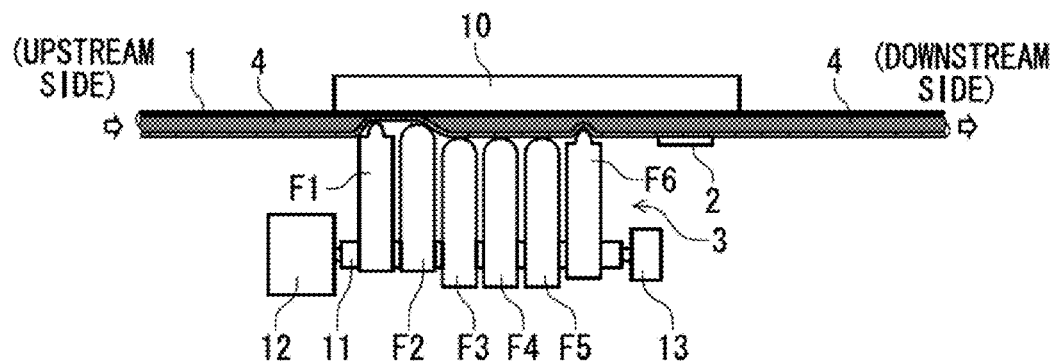
FIGS. 1A to 1C are schematic diagrams of the invention.
Figure 1B:
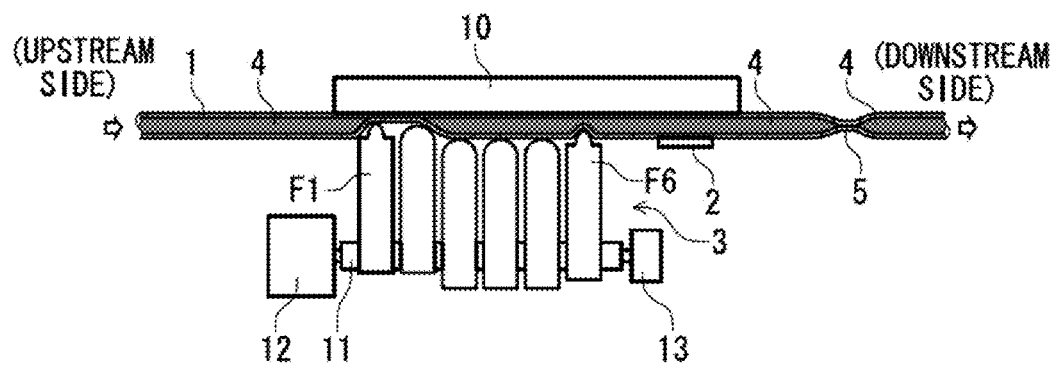
Figure 1C:
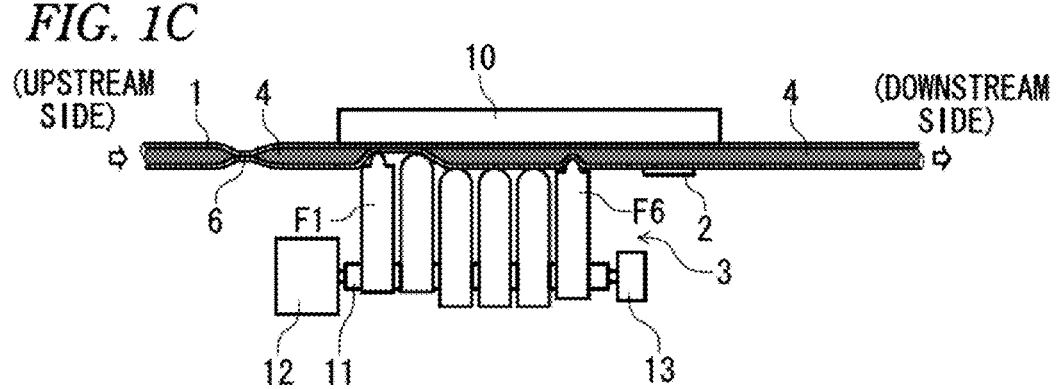

In the invention, as shown in FIGS. 1A to 1C, an occlusion on the upstream and downstream sides of a tube (fluid path, tubular body) 1 can be detected by using a single occlusion sensor 2 which is disposed on the downstream side of a pump mechanism 3, or namely by a configuration where an occlusion sensor is not disposed on the upstream side. Hereinafter, principle of the detection of occlusion will be described. In FIGS. 1A to 1C, 10 denotes a pressing plate which holds the tube 1 by pressing the tube 1 toward the pump mechanism 3. The pressing plate 10 is a member which allows the liquid transporting operation of the pump mechanism 3 to be normally performed, and which enables the occlusion sensor 2 to correctly detect a deformation of the outer shape of the tube 1.

FIG. 1A shows the normal state where an occlusion does not occur on both the upstream and downstream sides of the pump mechanism 3, namely a transfusion 4 is smoothly transported through the tube 1.

In the normal state, when an occlusion occurs somewhere of the tube 1 on the downstream side, for example, in a position 5, the internal pressure of the portion of the tube 1 which is on the upstream side of the occlusion position 5 rises higher than that in the normal state, and the tube 1 is inflated (externally deformed) [FIG. 1B]. This causes the occlusion sensor 2 which is disposed on the downstream side, to be pressed, and an output signal (tube internal pressure detection signal) is changed, with the result that the rise of the internal pressure of the portion of the tube 1 which is on the downstream side is detected, namely the occlusion on the downstream side is detected.

In the case where an occlusion sensor is disposed also on the upstream side as in the prior art technique, when an occlusion occurs on the upstream side, the transfusion is not replenished to the downstream side of the occlusion position. Therefore, the tube is contracted more than that in the normal state. This causes the occlusion sensor which is disposed on the upstream side to detect the lowering of the internal pressure occurring in the tube, namely, the occlusion on the upstream side is detected.

In the present invention, by contrast, also an occlusion on the upstream side can be detected by the occlusion sensor 2 which is disposed on the downstream side, as described below.

First, the liquid transporting operation will be described with reference to FIGS. 2A to 2F which show the pump mechanism 3 of the finger type which is one kind of peristaltic type.

FIGS. 2A to 2F are views showing relationships between fingers F (F1 to F6) during the liquid transporting operation and the press-closed state of the tube 1, and more specifically one cycle of a peristaltic motion (liquid transporting operation) which is caused by advancing/retracting operations of the six fingers F1 to F6, and which is applied to the tube 1. In the fingers F1 to F6, the fingers F2 to F5 are used for liquid transporting, and the fingers F1, F6 are used for storing the transfusion 4 in the tube 1. In the figures, the upper side in the tube 1 is pressed by the pressing plate 10 [see FIGS. 1A to 1C].

One cycle of a peristaltic motion will be described.

Returning to FIG. 2A, the finger F6 which is at the downstream end of the pump mechanism 3 (the downstream end of the tube in the pump mechanism 3) is advanced to the most advanced position to block the transfusion flow, and the transfusion 4 is supplied into the tube 1 of the pump mechanism 3.

Figure 2A:
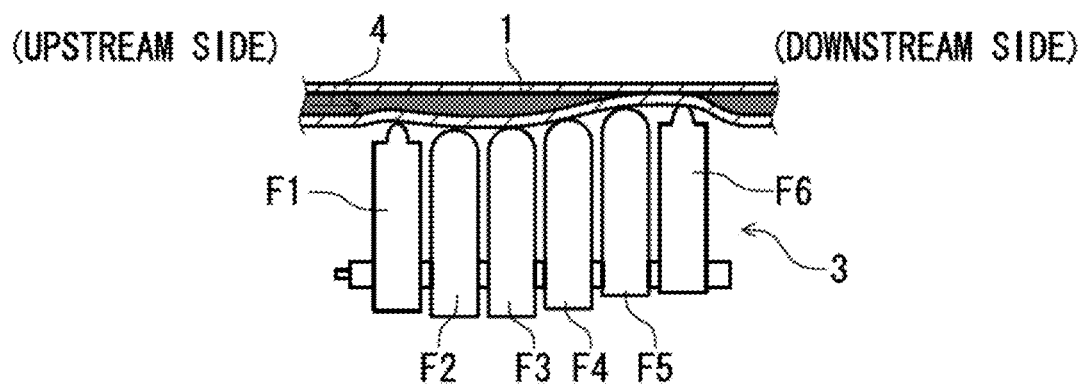
FIGS. 2A to 2F are operation diagrams of a pump mechanism in the invention.
Figure 2B:
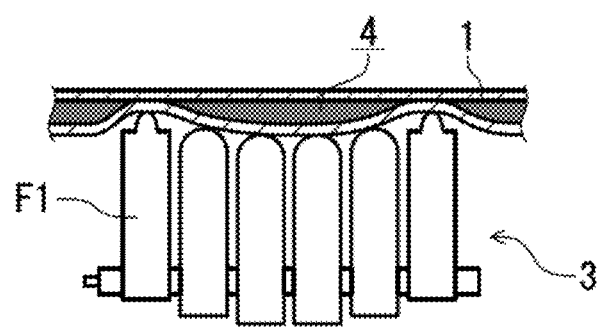

In FIG. 2B, the finger F1 is advanced to the most advanced position to block the transfusion flow also at the upstream end of the pump mechanism 3 (the upstream end of the tube in the pump mechanism 3), and the transfusion 4 is stored in the tube 1, thereby preparing for liquid transporting.

Figure 2C:
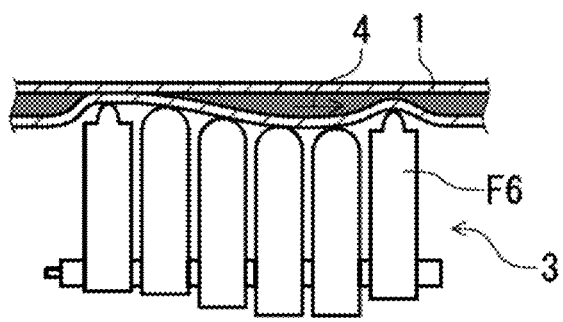

In FIG. 2C, the finger F6 begins to be retracted to start liquid transporting toward the downstream side in the tube.

Figure 2D:
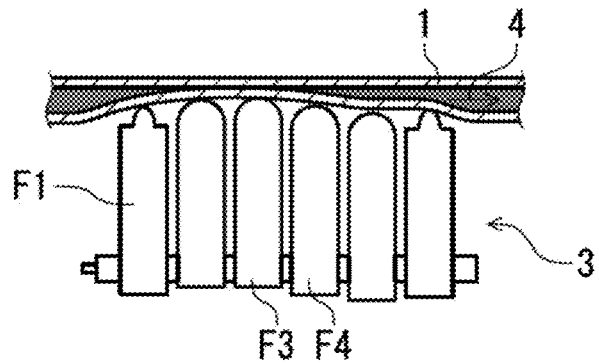

In FIG. 2D, the fingers F3, F4 are advanced to sequentially transport the transfusion toward the downstream side in the tube. Furthermore, the finger F1 begins to be retracted, and the new transfusion 4 is collected in the tube 1.

Figure 2E:
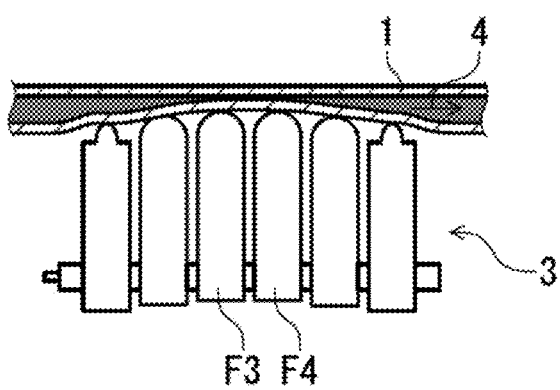

In FIG. 2E, subsequent to the finger F3, also the finger F4 is advanced to the most advanced position, the liquid transporting toward the downstream end side in the tube remains to be performed, and the collection of the new transfusion 4 in the tube 1 is continued.

Figure 2F:
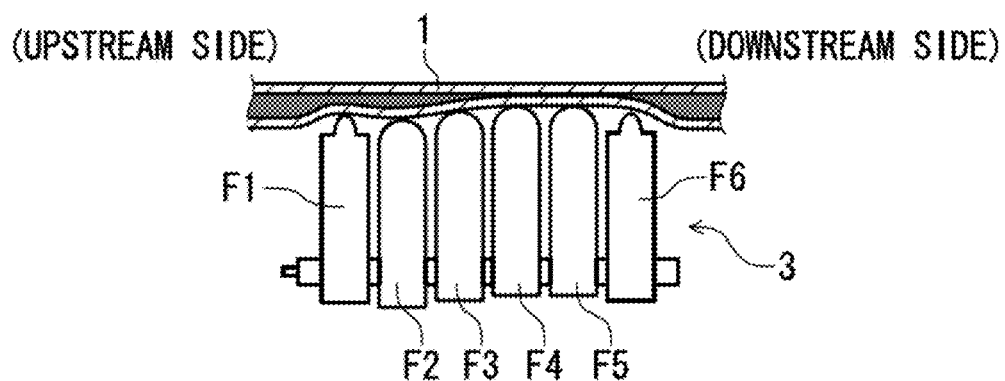

In FIG. 2F, subsequent to the finger F4, also the finger F5 is advanced to the most advanced position to complete the ejecting operation, and the one cycle of the peristaltic motion ends and returns to the state of FIG. 2A. FIG. 2F shows also a stage prepared for the next liquid transporting.

By repeating the states of FIGS. 2A to 2F, the peristaltic motion is continued.

Figure 3A:
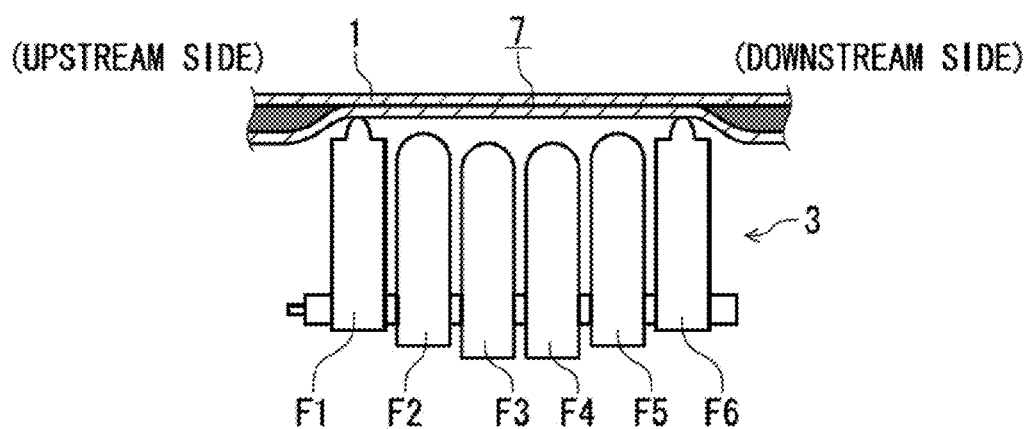
FIGS. 3A and 3B are operation diagrams in the case where an occlusion occurs on the upstream side in the invention.
Figure 3B:
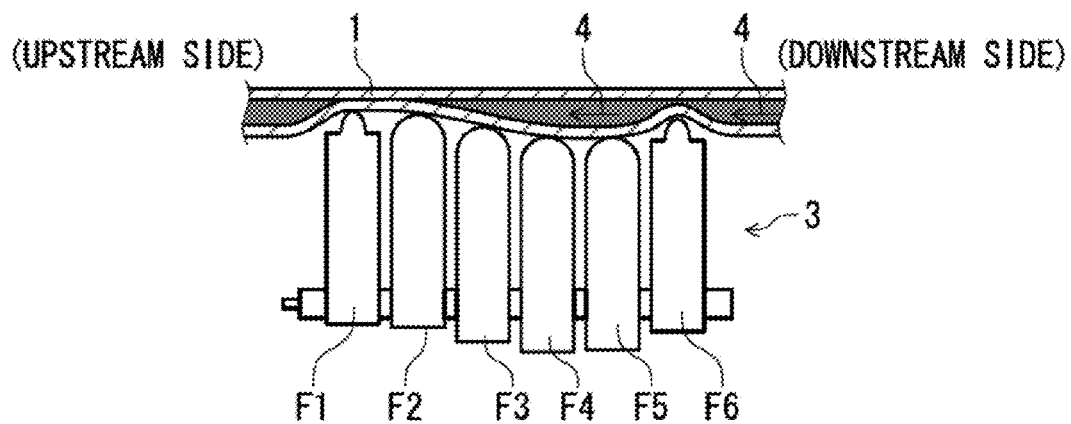

In FIG. 1C position 6 for example, it is assumed that an occlusion occurs somewhere in the tube 1 on the upstream side. The amount of the transfusion in a portion extending from the occlusion position 6 to the pump mechanism 3 is gradually reduced as compared with that in the normal state. The timing state displayed in FIG. 2B, shows that the transfusion 4 is not stored in the tube 1, and, in the portion where the transfusion 4 originally exists, the internal pressure is reduced, and the tube 1 is in a collapsed state as shown in FIG. 3A. In this state, at the moment when the finger F6 is retracted and the downstream end of the pump mechanism 3 is opened as shown in FIG. 3B [corresponding to FIG. 2C], the transfusion 4 flows in reverse from the downstream side toward the portion 7 where the transfusion 4 does not exist and the tube 1 is collapsed, and the portion of the tube 1 on the downstream side is contracted.

In accordance with the process of the transfusion 4 flowing in reverse and the subsequent contraction of the tube 1, although the scale is small as compared with the occlusion on the downstream side shown in FIG. 1B, the outer shape is deformed. It is possible to detect the occlusion of the tube 1 on the upstream side when the occlusion sensor 2 [FIG. 1C] disposed on the downstream side of the pump mechanism 3 detects the deformation of the outer shape of the tube 1.

During the liquid transporting operation (the series of peristaltic motions by the fingers F) of the pump mechanism 3, the deformation of the outer shape of the tube 1 is caused at the timing when the state of FIG. 2B is changed to that of FIG. 2C, in each cycle, i.e., in synchronization with the liquid transporting operation by the pump mechanism 3. Thus, the processor can detect that the occlusion has occurred on the upstream side of the pump mechanism based on a change in an output signal of the occlusion sensor based on the deflation of the flexible tube occurring in synchronization with a cycle of a transportation movement of the pump mechanism.

As a mechanism for driving the fingers F (F1 to F6), a configuration is usually used in which, as shown in FIGS. 1A to 1C, the fingers F are engaged with eccentric cams, and an eccentric cam shaft 11 on which the eccentric cams are disposed is rotated by a motor 12. In this case, in order to monitor the operation of the motor, the rotational position of the motor 12 is detected by a rotational position sensor 13 such as an optical encoder. By referring to the output signal (rotation position signal) of the rotational position sensor 13 of the motor 12, therefore, it is possible to determine in which one of the liquid transporting operation states shown in FIGS. 2A to 2F the fingers F currently exist.

According to the configuration, also in the output signal of the occlusion sensor 2, a change is caused in synchronization with the output signal of the rotational position sensor 13. Even when the level of the output signal is relatively low, therefore, it is possible to analyze the existence/non-existence of a change in the signal.

As described above, it has been found that, when a change of the output signal of the occlusion sensor 2 occurs in synchronization with the output signal of the rotational position sensor 13 of the motor 12, the change is caused by an occlusion on the upstream side. Therefore, an occlusion on the upstream side can be detected by the occlusion sensor 2 [FIGS. 1A to 1C] which is disposed on the downstream side.

A contraction of the tube 1 caused by an occlusion on the upstream side occurs periodically or in each cycle of the liquid transporting operation. Alternatively, in the case where a periodical change occurs in the output signal of the occlusion sensor 2, therefore, an occlusion on the upstream side may be detected based on the period of the change.

Moreover, it is possible to detect not only an occlusion occurring in the tube 1, but also a state where the transfusion 4 does not exist (the state where the transporting of the whole amount of the transfusion 4 is completed).

A driving source operation position sensor which is usually used in the control of a driving source for driving the pump mechanism 3, in the embodiment, the rotational position sensor 13 which is usually used in the control of the motor 12 can be used also as the rotational position sensor 13 which is necessary for detecting a change which is produced in the output signal of the occlusion sensor 2 in synchronization with the liquid transporting operation. Therefore, it is not necessary to dispose an additional device as the rotational position sensor.

Figure 4:
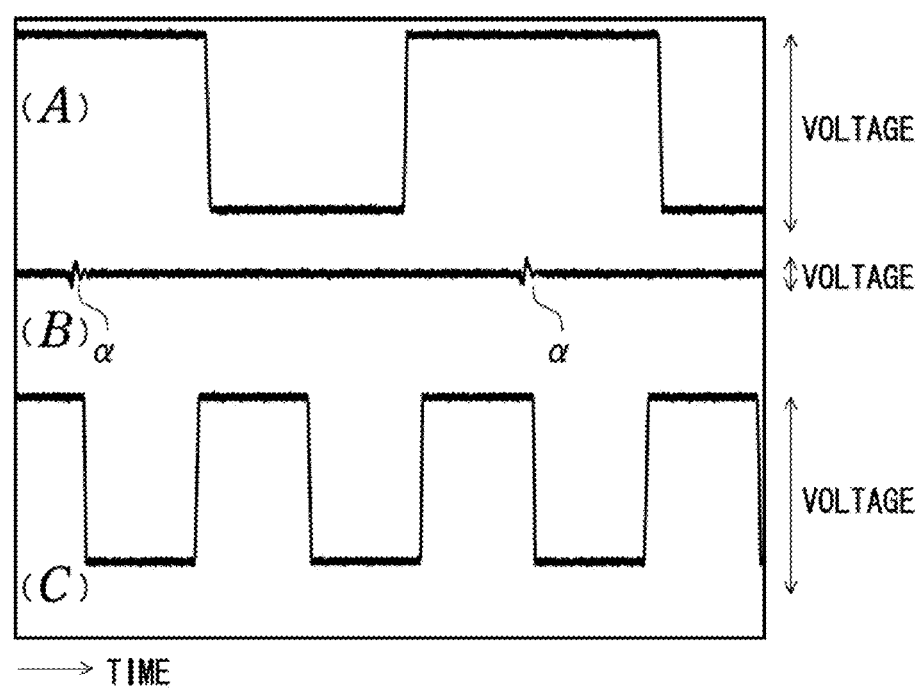
FIG. 4 is a time chart showing an output signal of a downstream occlusion sensor and that of a rotational position sensor in the case where an occlusion occurs on the upstream side of the pump mechanism in the invention.

FIG. 4 is a time chart showing the output signal of the occlusion sensor 2 disposed on the downstream side, and that of the rotational position sensor 13 in the case where an occlusion occurs on the upstream side. The shown output signals were actual measurements. In the measurement, a rotational position sensor having two sensor sections was used as the rotational position sensor 13.

In FIG. 4, (A) shows an output signal of one of the sensor sections of the rotational position sensor 13, (B) shows the output signal of the occlusion sensor 2 disposed on the downstream side, and (C) shows an output signal of the other sensor section of the rotational position sensor 13.

In the output signal of the occlusion sensor 2 shown in (B) of FIG. 4, oscillatory waveform portions indicated by the reference letter α show signals appearing due to an occlusion occurring on the upstream side. It is seen that the oscillatory waveform portions α are periodically generated in synchronization with a specific rotational position of the output signals of the rotational position sensor 13 (the both sensor sections) shown in (A) and (C) of FIG. 4.

The rotational position sensor 13 including the two sensor sections which output the rotation position signals [(A) and (C) of FIG. 4] in different periods was used in order to identify the rotational direction (normal or reverse rotational direction) of the motor 12. In the case where only the detection of the rotational position is required, such as in specifications in which the reverse rotation of the motor 12 is disabled, a rotational position sensor including one sensor section may detect an occlusion on the upstream side. The method of identifying the rotational direction of a motor or the like by using the rotational position sensor 13 including two sensor sections which output rotation position signals at different periods is well known. Therefore, the description of the method is omitted.

Figure 5:
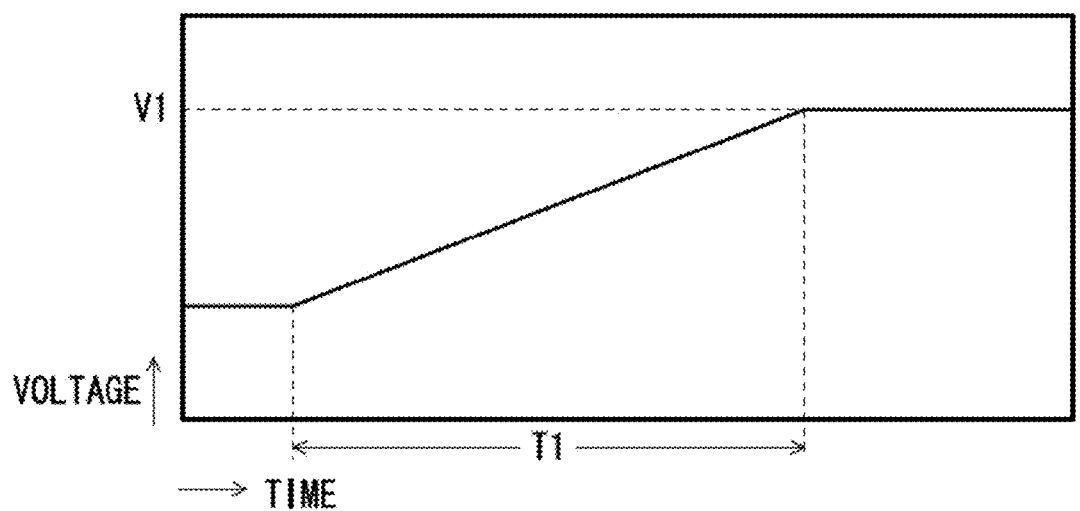
FIG. 5 is a time chart showing an output signal of a downstream occlusion sensor in the case where an occlusion occurs on the downstream side.

FIG. 5 shows the signal which, in the case where an occlusion occurs on the downstream side as shown in FIG. 1B, is output from the occlusion sensor 2 disposed on the downstream side. In this case, during the period when the pump mechanism 3 continues the liquid transporting operation after the occurrence of the occlusion, the output signal level of the occlusion sensor 2 continuously rises substantially in proportion to the elapsed time. Therefore, an occlusion occurring on the downstream side can be detected when the output signal level of the occlusion sensor 2 reaches a given signal level V1, it is assumed that an occlusion occurs on the downstream side. The signal level V1 is arbitrarily set in accordance with the detection accuracy. Alternatively, several different signal levels may be previously set, and one of the levels may be selected.

In a similar manner as the prior art detection method performed by an occlusion sensor which is disposed on the downstream side, as described above, an occlusion occurring on the downstream side can be detected simply by, after the output signal level of the occlusion sensor 2 begins to rise, performing a comparison whether the output signal level of the occlusion sensor 2 exceeds the predetermined threshold (signal level) V1 or not. Therefore, the rotation position signal of the above-described rotational position sensor 13 is not necessary.

According to the invention, as described above, occlusions on the upstream and downstream sides in the tube 1 can be detected by using only the occlusion sensor 2 which is disposed on the downstream side of the pump mechanism 3, i.e., the single occlusion sensor 2, and hence the production cost and size of the occlusion detection device can be reduced.

The occlusion sensor 2 may be a sensor other than a strain gauge as far as it can detect the rise of the internal pressure of the tube 1, particularly a deformation of the outer shape of the tube 1 caused by the rise of the internal pressure. In the case were a strain gauge is used as the occlusion sensor 2, the surface portion of the sensor can be made flat, and therefore the ability to clean it can be improved. A strain gauge further has a feature that the output is stable against a temperature change.

Hereinafter, embodiments of the invention will be described with reference to the drawings. In the figures, the same reference numerals denote identical or equivalent components.

Figure 6:
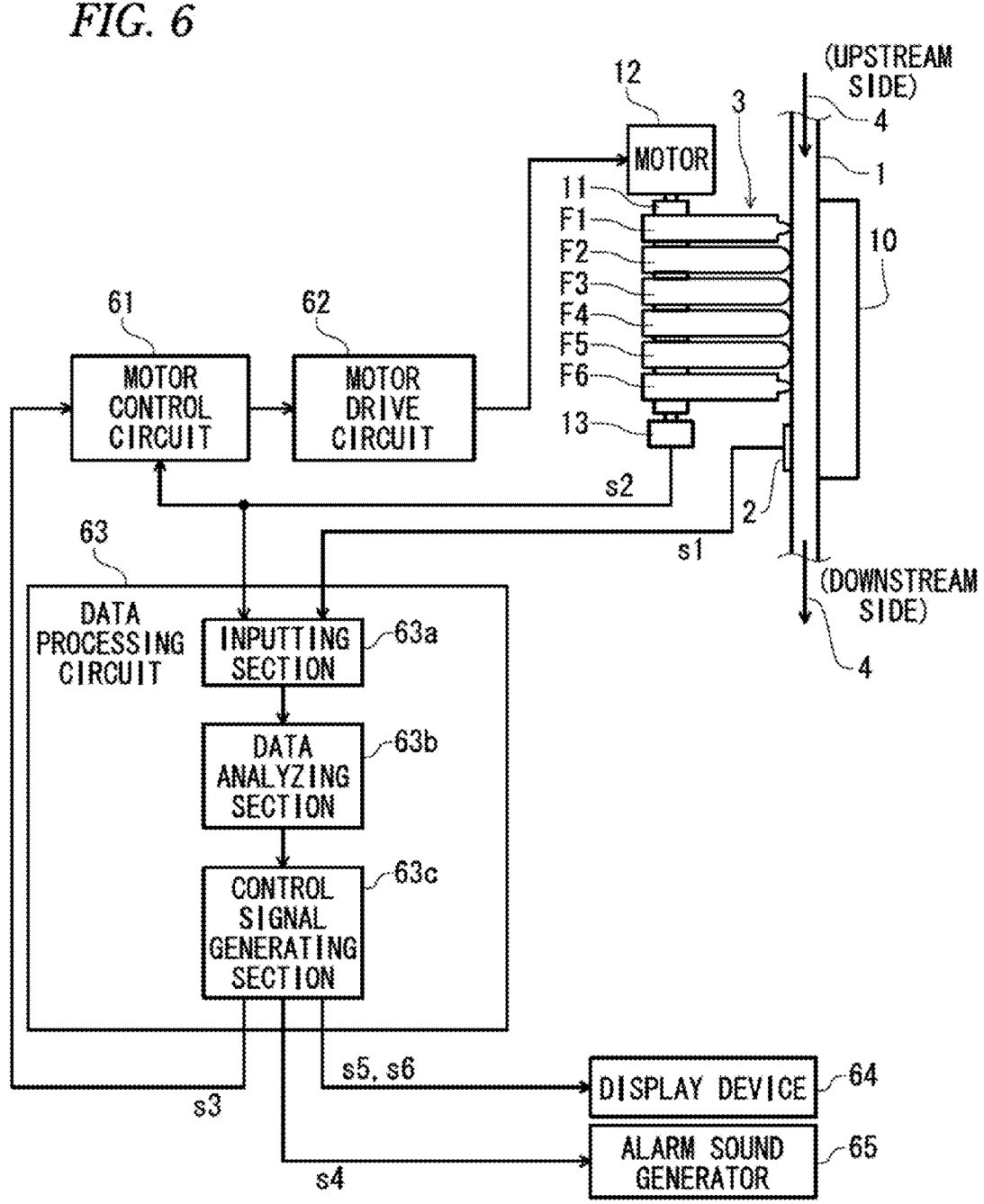
FIG. 6 is a block diagram of an embodiment of the occlusion detection device of the present invention.

FIG. 6 is a block diagram of an embodiment of the occlusion detection device of the invention.

In FIG. 6, 61 denotes a motor control circuit that controls a motor drive circuit 62 so as to drive the motor 12 to cause the pump mechanism 3 to perform the liquid transporting operation, thereby transporting the transfusion 4 in the tube 1 from the upper side in FIG. 6 toward the lower side.

A stepping motor is used as the motor 12. The rotation position signal (driving source operation position signal) s2 output from the rotational position sensor 13 is fed back to the motor control circuit 61 so that the motor 12 can be controlled highly accurately.

A data processing circuit 63 receives the output signal (tube internal pressure detection signal) s1 of the occlusion sensor 2, and the rotation position signal s2 output from the rotational position sensor 13, and detects an occlusion of the tube 1. Specifically, the data processing circuit 63 analyzes the existence/non-existence of an occlusion of the tube 1, which side of the upstream and downstream sides of the pump mechanism 3 the occlusion occurs, and outputs a result of the analysis.

In the embodiment, the data processing circuit 63 includes an inputting section 63a, a data analyzing section 63b, and a control signal generating section 63c.

The inputting section 63a of the data processing circuit 63 applies a necessary input process which corresponds to the output signal s1 of the occlusion sensor 2, and the rotation position signal s2 output from the rotational position sensor 13, such as an amplification, a waveform shaping, and an A/D conversion to the signals s1, s2. The data analyzing section 63b performs the above-described analysis, and gives the analysis result (result of the occlusion detection) to the control signal generating section 63c. Based on the analysis result supplied from the data analyzing section 63b, the control signal generating section 63c outputs control signals s3 to s6 corresponding to the use.

A display device 64 and an alarm sound generator 65 are connected to the occlusion detection device of the embodiment. When an occlusion is detected, the display device displays a warning message, and the alarm sound generator generates an alarm sound. The display device 64 and the alarm sound generator 65 are connected to an output terminal of the control signal generating section 63c of the data processing circuit 63. The output terminal of the control signal generating section 63c is connected also to the motor control circuit 61 so that the motor 12 is stopped when an occlusion is detected.

As described above, the occlusion sensor 2 is disposed only on the downstream side of the pump mechanism 3, and occlusions on the upstream and downstream sides in the tube 1 can be detected.

Figure 7:
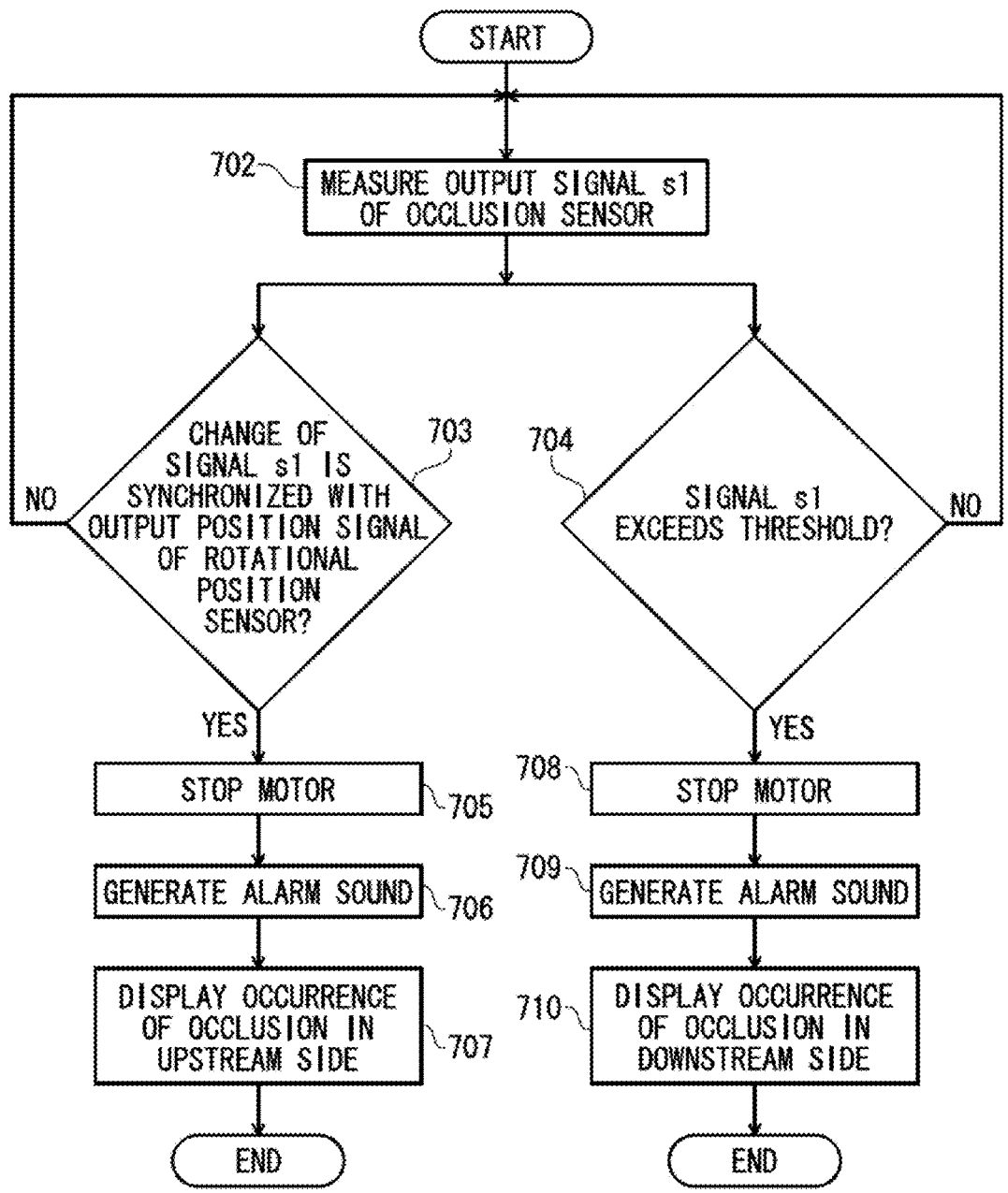
FIG. 7 is a flowchart illustrating the operation of the occlusion detection device according to the present invention.

Next, the operation of the embodiment will be described with reference to the flowchart of FIG. 7.

The motor control circuit 61 controls the motor drive circuit 62 to drive the motor 12, the pump mechanism 3 is performing the liquid transporting operation shown in FIGS. 2A to 2F, and the transfusion 4 is transported in the tube 1 from the upper side in FIG. 6 toward the lower side.

In the state of the liquid transporting operation, the output signal s1 of the occlusion sensor 2, and the rotation position signal s2 output from the rotational position sensor 13 are fetched into the inputting section 63a of the data processing circuit 63 (step 702).

The data analyzing section 63b which receives the output signal from the inputting section 63a executes steps 703 and 704.

In step 703, it is determined whether the change of the output signal s1 of the occlusion sensor 2, specifically, the oscillatory waveform portions α in FIG. 4B are synchronized with the rotation position signal s2 output from the rotational position sensor 13 or not ("Yes" or "No"), i.e., whether an occlusion on the upstream side in the tube 1 occurs or not. The determination of "Yes" indicating that an occlusion occurs is performed in the case where the change of the output signal s1 of the occlusion sensor 2 is caused at a specific timing of the rotation position signal s2 (the moment when the state of FIG. 2C is produced). Thus, the occlusion detection device will output the analysis result of an occlusion detection indicating that an occlusion position in the fluid path is on the upstream side of the pump mechanism when determined, based on the output signal of the position sensor and the output signal of the occlusion sensor, that the deflation of the fluid path is detected by the occlusion sensor in synchronization with a time point at which the operation position of the driving source of the pump mechanism is changed from a first state in which a downstream side of the fluid path is closed by the pump mechanism to a second state in which the downstream side of the fluid path is opened by the pump mechanism.

If the result of the determination in step 703 is "No", the process returns to step 702, and, if "Yes", steps 705 to 707 are executed.

In step 705, the control signal generating section 63c outputs the signal s3 for stopping the motor 12 to the motor control circuit 61, thereby stopping the motor 12.

In step 706, the control signal generating section 63c outputs the signal s4 indicating that an occlusion occurs in the tube 1, to the alarm sound generator 65, thereby causing the alarm sound generator 65 to generate the alarm sound. In step 707, the control signal generating section 63c outputs the signal s5 indicating that an occlusion occurs on the upstream side in the tube 1, to the display device 64, thereby causing the display device 64 to display, for example, an alarm message "Occlusion occurs in upstream side!!".

The operator is informed of the situation where an occlusion occurs in the tube 1, by the alarm sound generated by the alarm sound generator 65, and also of that where the occlusion occurs on the upstream side, by the alarm message displayed on the display device 64.

The sequence of steps 706 and 707 may be reversed.

In step 704, it is determined whether the change of the output signal s1 of the occlusion sensor 2, specifically, the level of the output signal of the occlusion sensor 2 shown in FIG. 5 exceeds the threshold (signal level) V1 or not ("Yes" or "No"), i.e., whether an occlusion on the downstream side in the tube 1 occurs or not. Alternatively, several kinds of thresholds (signal levels) V1 may be prepared, and a step in which the operator selects one of them may be set, for example, at a time before the execution of the flowchart of FIG. 7.

If the result of the determination in step 704 is "No", the process returns to step 702, and, if "Yes", steps 708 to 710 are executed.

In step 708, the control signal generating section 63c outputs the signal s3 for stopping the motor 12 to the motor control circuit 61, thereby stopping the motor 12.

In step 709, the control signal generating section 63c outputs the signal s4 indicating that an occlusion occurs in the tube 1, to the alarm sound generator 65, thereby causing the alarm sound generator 65 to generate the alarm sound.

In step 710, the control signal generating section 63c outputs the signal s6 indicating that an occlusion occurs on the downstream side in the tube 1, to the display device 64, thereby causing the display device 64 to display, for example, an alarm message "Occlusion occurs in downstream side!!".

The operator is informed of the situation where an occlusion occurs in the tube 1, by the alarm sound generated by the alarm sound generator 65, and also of that were the occlusion occurs on the downstream side, by the alarm message displayed on the display device 64.

The sequence of steps 709 and 710 may be reversed.

The alarm sound generator 65 may generate different kinds of alarm sounds depending on whether the occlusion occurs on the upstream side of the pump mechanism 3 or on the downstream side, so that the position of occurrence of the occlusion can be known also from the kind of the alarm sound.

If both the results of the determinations in steps 702 to 704 are "No", it may be determined that an occlusion does not occur in both the upstream and downstream sides of the pump mechanism 3, and a message indicating a normal state may be displayed on the display device 64.

In the embodiment, based on the finding that, in the case where a change of the output signal of the occlusion sensor 2 occurs in synchronization with the output signal of the rotational position sensor 13, the change is caused by an occlusion on the upstream side, as described above, an occlusion on the upstream side is detected by the occlusion sensor 2 which is disposed on the downstream side. An occlusion on the downstream side can be easily detected by detecting a deformation of the outer shape of the tube 1 that is disposed on the downstream side, the deformation being due to inflation of the tube, by the occlusion sensor 2 which is disposed on the downstream side.

According to the embodiment, therefore, occlusions on the upstream and downstream sides can be detected by the occlusion sensor 2 which is disposed on the downstream side. Consequently, the number of components and the number of assembling steps can be decreased to lower the production cost, and the space occupied by the components can be reduced, whereby the size of the device can be made small.

Next, an embodiment of the transfusion apparatus including the occlusion detection device will be described with reference to FIG. 8.

Figure 8:
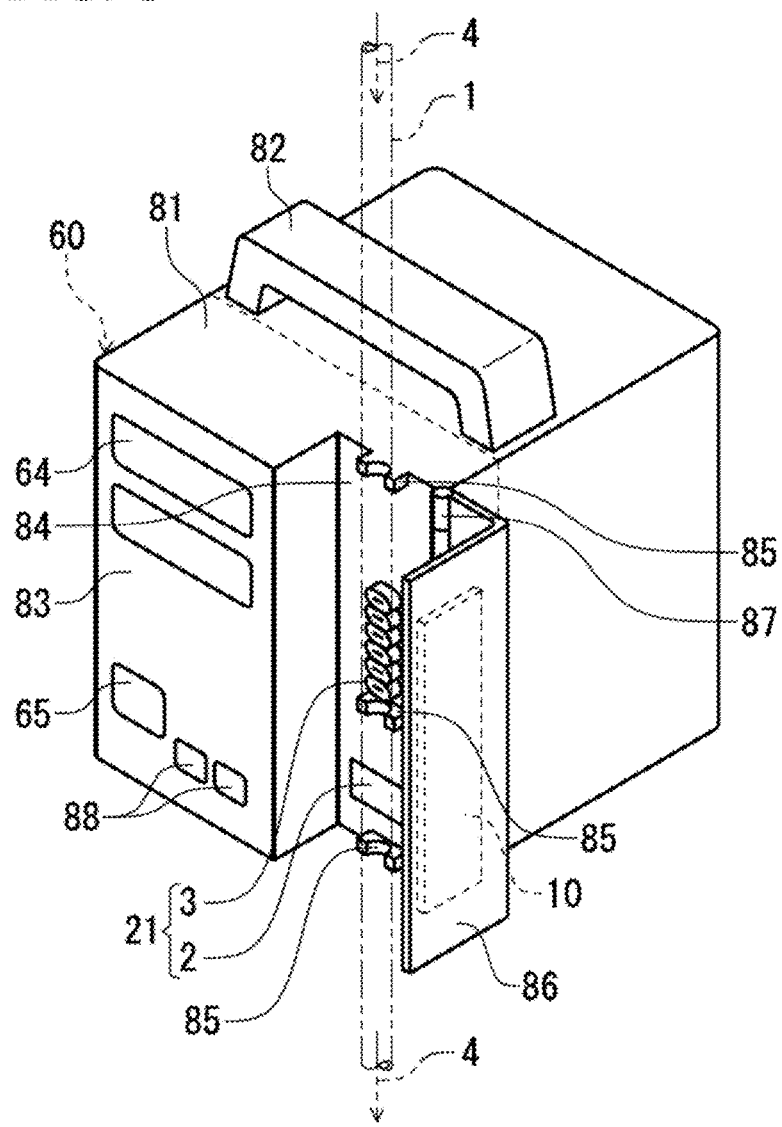
FIG. 8 is a perspective view showing an embodiment of the transfusion apparatus including the occlusion detection device shown in FIG. 6.

In FIG. 8, 81 denotes a housing in which a handle 82 is disposed on the upper surface. The housing 81 houses: a transfusion apparatus body configured by the pump mechanism 3, and driving, controlling, data processing means, and alarming means which are related to the operation of the transfusion apparatus, and which are not shown; and the above-described occlusion detection device, in the embodiment, the occlusion detection device 60 shown in FIG. 8.

The motor control circuit 61, motor drive circuit 62, display device 64, and alarm sound generator 65 which are related to the liquid transporting operation of the pump mechanism 3, and which are shown in FIG. 6 are included in the transfusion apparatus body. The data processing means of the transfusion apparatus body may function also as the data processing circuit 63 in FIG. 6.

The occlusion sensor 2 which is disposed on the downstream side of the pump mechanism 3 as shown in FIG. 6 is the only one which is disposed in the occlusion detection device 60. Occlusions on the upstream and downstream sides in the transfusion tube 1 are detected by the single occlusion sensor 2.

A substantially left half of the front of the housing 81 is formed as an operation panel 83. A pump mechanism placement surface 84 is formed in a position which is in the right half front, and which is retracted toward the back surface. The pump mechanism 3 and the occlusion sensor 2 are disposed in the pump mechanism placement surface 84. The occlusion sensor 2 is positioned immediately below the pump mechanism 3.

A transfusion tube guide 85 is disposed in each of a plurality (in the embodiment three) of places which are vertically arranged in the pump mechanism placement surface 84. The transfusion tube guides 85 guide and hold the transfusion tube 1 which vertically elongates while passing over the surface of the portions of the pump mechanism 3 and the occlusion sensor 2 (pump/sensor section 21), to a predetermined position.

A door 86 which covers the pump mechanism placement surface 84 is disposed on the housing 81. The door 86 is openable and closable about a hinge 87.

The pressing plate 10 is attached to the rear surface of the door 86. The pressing plate 10 is a member which, when the door 86 is closed, holds the transfusion tube 1 by pressing the transfusion tube 1 attached to the surface of the pump/sensor section 21, in cooperation with the pump/sensor section 21, which allows the liquid transporting operation of the pump mechanism 3 to be normally performed, and which enables the occlusion sensor 2 to correctly detect a deformation of the outer shape of the transfusion tube 1.

A plurality of switches (switch group 88) which are used for operating the transfusion apparatus, such as a power switch, a liquid transport start switch, a liquid transport stop switch, a forced stop switch, and an alarm sound/message stop switch are disposed in the operation panel 83 in the left side of the front of the housing 81. Also the display device 64, the alarm sound generator 65, and the like which are shown in FIG. 6 are disposed in the panel, so that displays of various operation conditions of the transfusion apparatus, generation of the alarm sound, a display of the alarm message, and like are enabled.

In the configuration, in a state where the transfusion tube 1 is attached onto the pump/sensor section 21 while being held by the transfusion tube guides 85, and the door 86 is closed, the switch group 88 on the operation panel 83 is operated to start the liquid transporting operation of the pump mechanism 3.

When the occlusion detection device 60 detects an occlusion of the transfusion tube 1 during the liquid transporting operation, the pump mechanism 3 is automatically stopped to ensure the safety. The alarm sound generator 65 generates the alarm sound, and the alarm message is displayed on the display device 64. The contents of the alarm message are changed depending on whether the occlusion occurs on the upstream side of the pump mechanism 3 or on the downstream side. When the operator views the alarm message, therefore, the operator can know the occlusion occurring position, and deal with the occlusion depending on the occurring position.

In the transfusion apparatus, the occlusion detection device 60 which can be produced at a low cost, and which is small in size is used as an occlusion detection device for the transfusion tube 1. Therefore, the production cost and size of the occlusion detection device can be reduced.

What is claimed is:

1. An occlusion detection device that detects an occlusion of a flexible fluid path on either of upstream and downstream sides of a pump mechanism, the pump mechanism transporting a liquid through the fluid path by elastically deforming the fluid path, the occlusion detection device comprising:
an occlusion sensor that is disposed on the downstream side of the pump mechanism and detects an inflation or a deflation of the fluid path due to a change in an internal pressure of the fluid path during a liquid transporting operation of the pump mechanism;
a data processing circuit that analyzes on which side of the upstream and downstream sides of the pump mechanism the occlusion of the fluid path occurs, based on a change of the internal pressure of the fluid path detected by the occlusion sensor, and outputs an analysis result; and
a position sensor that detects a periodic operation position of a driving source of the pump mechanism,
wherein the pump mechanism is a peristaltic pump mechanism that transports the liquid by a peristaltic motion, and
wherein the data processing circuit is configured to:
receive an output signal of the position sensor and an output signal of the occlusion sensor;
output the analysis result of an occlusion detection indicating that an occlusion position in the fluid path is on the downstream side of the pump mechanism when determined, based on the output signal of the occlusion sensor, that the inflation of the fluid path is detected by the occlusion sensor; and
output the analysis result of an occlusion detection indicating that an occlusion position in the fluid path is on the upstream side of the pump mechanism when determined, based on the output signal of the position sensor and the output signal of the occlusion sensor, that the deflation of the fluid path is detected by the occlusion sensor in synchronization with a time point at which the operation position of the driving source of the pump mechanism is changed from a first state in which a downstream side of the fluid path is closed by the pump mechanism to a second state in which the downstream side of the fluid path is opened by the pump mechanism.

2. The occlusion detection device according to claim 1, wherein the fluid path is a tube.

3. The occlusion detection device according to claim 2, wherein the pump mechanism is a finger pump mechanism that transports the liquid by a peristaltic motion caused by advancing and retracting a plurality of fingers, or a roller pump mechanism that transports the liquid by a peristaltic motion caused by rotations of a plurality of rollers.

4. The occlusion detection device according to claim 1, wherein the occlusion sensor is a strain gauge that detects a deformation of an outer shape of the fluid path.

5. A transfusion apparatus comprising:
a pump mechanism that transports a liquid through a fluid path by elastically deforming the fluid path; and
an occlusion detection device that detects an occlusion of the fluid path on either of upstream and downstream sides of the pump mechanism, the occlusion detection device comprising:
an occlusion sensor that is disposed on the downstream side of the pump mechanism and detects an inflation or a deflation of the fluid path due to a change in an inflation or a deflation of the fluid path due to a change in an internal pressure of the fluid path during a liquid transporting operation of the pump mechanism;
a data processing circuit that analyzes on which side of the upstream and downstream sides of the pump mechanism the occlusion of the fluid path occurs, based on a change of the internal pressure of the fluid path detected by the occlusion sensor and outputs an analysis result; and
a position sensor that detects a periodic operation position of a driving source of the pump mechanism,
wherein the pump mechanism is a peristaltic pump mechanism that transports the liquid by a peristaltic motion, and
wherein the data processing circuit is configured to:
receive an output signal of the position sensor and an output signal of the occlusion sensor;
output the analysis result of an occlusion detection indicating that an occlusion position in the fluid path is on the downstream side of the pump mechanism when determined, based on the output signal of the occlusion sensor, that the inflation of the fluid path is detected by the occlusion sensor; and
output the analysis result of an occlusion detection indicating that an occlusion position in the fluid path is on the upstream side of the pump mechanism when determined, based on the output signal of the position sensor and the output signal of the occlusion sensor, that the deflation of the fluid path is detected by the occlusion sensor in synchronization with a time point at which the operation position of the driving source of the pump mechanism is changed from a first state in which a downstream side of the fluid path is closed by the pump mechanism to a second state in which the downstream side of the fluid path is opened by the pump mechanism.

6. The transfusion apparatus according to claim 5, wherein the fluid path is a transfusion tube.

* * * * *